(12) United States Patent
Spencer

(10) Patent No.: US 9,113,973 B2
(45) Date of Patent: Aug. 25, 2015

(54) METHOD OF REDUCTION OF PROXIMAL HUMERAL FRACTURE

(71) Applicant: Edwin E. Spencer, Knoxville, TN (US)

(72) Inventor: Edwin E. Spencer, Knoxville, TN (US)

( * ) Notice: Subject to any disclaimer, the term of this patent is extended or adjusted under 35 U.S.C. 154(b) by 145 days.

(21) Appl. No.: 14/041,001

(22) Filed: Sep. 30, 2013

(65) Prior Publication Data

US 2014/0031876 A1    Jan. 30, 2014

Related U.S. Application Data

(62) Division of application No. 12/463,656, filed on May 11, 2009, now Pat. No. 8,545,539.

(60) Provisional application No. 61/052,283, filed on May 12, 2008.

(51) Int. Cl.
*A61B 17/88* (2006.01)
*A61B 17/56* (2006.01)
*A61B 17/80* (2006.01)
(Continued)

(52) U.S. Cl.
CPC ............. *A61B 17/88* (2013.01); *A61B 17/02* (2013.01); *A61B 17/56* (2013.01); *A61B 17/8004* (2013.01); *A61B 17/8014* (2013.01); *A61B 17/8019* (2013.01); *A61B 17/8061* (2013.01); *A61B 17/8866* (2013.01); *A61B 17/025* (2013.01); *A61B 17/80* (2013.01); *A61B 2017/00915* (2013.01); *A61B 2017/564* (2013.01); *A61B 2017/565* (2013.01)

(58) Field of Classification Search
CPC ............. A61B 17/56; A61B 2017/564; A61B 2017/565; A61B 17/80; A61B 17/8004; A61B 17/8014; A61B 17/8019; A61B 17/8061; A61B 17/885; A61B 17/8866
See application file for complete search history.

(56) References Cited

U.S. PATENT DOCUMENTS

| 6,623,486 B1 | 9/2003 | Weaver et al. |
| 6,884,242 B2 | 4/2005 | LeHuec et al. |

(Continued)

FOREIGN PATENT DOCUMENTS

| EP | 1764053 A1 * | 3/2007 | ............. A61B 17/80 |
| FR | 2294685 | 7/1976 | |

(Continued)

OTHER PUBLICATIONS

International Search Report for PCT/EP2009/051030, dated Apr. 28, 2009.

*Primary Examiner* — Larry E Waggle, Jr.
(74) *Attorney, Agent, or Firm* — Knox Patents; Thomas A. Kulaga

(57) ABSTRACT

A method for reducing and fixing fractures, for example, a proximal humeral fracture. A jacking device is releasably attached to a locking plate that presses against an inferior aspect of the head to rotate the head into anatomic alignment. Suture material is stitched into the soft tissue superior to the head and pulls the superior end of the head and guides and steers the head. The suture material is passed through suture holes in the superior end of the plate. The jacking device is positioned to hold the head in an anatomic neck/shaft angle, thereby allowing the head to be fixed to the locking plate. In one such embodiment, a swivel bushing in the plate receives the jacking device and allows the angle of the device to be adjusted as desired. To aid in the fluoroscopic visualization during surgery, a radiolucent retractor is used to avoid blocking the surgeon's view.

20 Claims, 5 Drawing Sheets

(51) Int. Cl.
  *A61B 17/02*   (2006.01)
  *A61B 17/00*   (2006.01)

(56) References Cited

U.S. PATENT DOCUMENTS

2002/0026101 A1  2/2002  Bookwalter et al.
2004/0147812 A1  7/2004  Hamel
2005/0165395 A1*  7/2005  Orbay et al. ............... 606/60
2006/0089647 A1  4/2006  Culbert et al.
2006/0235399 A1  10/2006  Carls
2009/0281578 A1  11/2009  Spencer et al.
2009/0326591 A1*  12/2009  Spencer, Jr. ............... 606/282

FOREIGN PATENT DOCUMENTS

FR    2483214    12/1981
FR    0852803    8/2009
WO    2009095451    8/2009

* cited by examiner

METHOD OF REDUCTION OF PROXIMAL HUMERAL FRACTURE

CROSS-REFERENCE TO RELATED APPLICATIONS

This application is a divisional of prior application Ser. No. 12/463,656, filed May 11, 2009, which claims the benefit of U.S. Provisional Application No. 61/052,283, filed May 12, 2008.

STATEMENT REGARDING FEDERALLY SPONSORED RESEARCH OR DEVELOPMENT

Not Applicable

BACKGROUND OF THE INVENTION

1. Field of Invention

This invention pertains to a method for reduction and fixation of fractures, such as a proximal humeral fracture.

2. Description of the Related Art

Reducing a proximal humeral fracture requires that the proximal ends of the fracture by brought together and fixed. One technique for reducing and fixing such fractures is intramedullary nailing. Often intramedullary nailing results in inadequate fixation in the osteoporotic humeral head. Also, insertion of the intramedullary nail requires the surgeon to split the rotator cuff and destroy a portion of the superior aspect of the humeral head articular cartilage. Although intramedullary nailing may be effective in certain types of fractures, the damage to the rotator cuff and articular surface of the humeral head often outweighs the benefits of intramedullary nailing.

Closed reduction and percutaneous pinning is another technique for reducing and stabilizing proximal humeral fractures. The closed reduction avoids using an incision to access the fractured bones. The fracture is reduced by manual manipulation of the body. With the fracture reduced, metal pins or wires are inserted though the skin to fix and immobilize the fracture. The percutaneous pinning is often not well tolerated by patients, and the technique requires patient compliance to ensure a successful outcome.

Another technique for reducing and fixing proximal humeral fractures uses a plate that is fixed proximate to and bridging the fracture. The plate, commonly called a bone plate, is a rigid structure fixed to the head and the diaphysis after the fracture is reduced. The plate is attached to the bone by screws. Typically, the fracture is reduced by manually manipulating the head through an incision to move the head out of varus or other malalignment. The head is provisionally pinned and then the bone plate is fixed around the provisional fixation. Manual manipulation of the head oftentimes requires an enlarged incision to provide access to the head and, also, often results in damage to the soft tissue surrounding the head. Fixing the bone plate often results in soft tissue stripping. Although the bone plate potentially is capable of fixing the head and diaphysis after reduction, it is often difficult to reduce the fracture and maintain alignment while the bone plate is being fixed in place.

BRIEF SUMMARY OF THE INVENTION

The treatment of proximal humeral fractures in shoulder surgery is aided with a stable construct that sustains early mobilization with high healing rates and low complication rates. A plate bridging the fracture between the head and the shaft of the humerus aids in fixation, but the head must be reduced before fixation.

In accordance with the invention, for a proximal humeral fracture fixed with a locking plate, pushing the head from an inferior aspect to rotate the head to reduce the fracture allows for positioning the head out of varus or other malalignment, obviating the need for multiple pins to provisionally reduce the fracture, and minimizing the soft tissue stripping. The humerus is reduced by pushing the head out of varus or other malalignment, thereby allowing fixation.

In one embodiment of a fracture reduction and fixation device, a jacking device pushes an inferior aspect of the head. Simultaneously, sutures pull the superior aspect of the head. After the head rotates into alignment, a locking plate is attached to the head and the jacking device is removed. In one such embodiment, the jacking device engages a threaded opening in the plate. In another such embodiment, the jacking device engages a swivel bushing or other variable angle screw fixation device in the plate that allows precise angular positioning of the jacking device.

Proximal humeral fracture reduction and fixation is commonly performed with fluoroscopic visualization to aid in positioning and locating the various appliances as required. A radiolucent retractor allows access through soft tissue during reduction and fixation of the fracture, thereby allowing a scanner to "see" the humerus and the tools and appliances for reducing the fracture without being blocked by the retractor used to reduce the fracture.

An apparatus for treating a proximal humeral fracture, the apparatus comprising: a plate with a plurality of openings for receiving locking screws, the locking screws for attaching the plate to a humerus; and a jacking device for pushing the head of the humerus, the jacking device releasably attachable to the plate at a specified angle. In one such embodiment, the jacking device includes a jacking screw engaging a collar configured to screw into an opening in the plate. In one embodiment, the opening in the plate that receives the jacking device includes a swivel bushing that allows the angle of the jacking screw to be adjusted. In another such embodiment, the plate includes a plurality of holes for receiving suture material, the plurality of holes positioned along the margin of the plate. Although the apparatus and method is described with respect to the treatment of proximal humeral fractures, the apparatus and method is applicable to treatment of other types of fractures.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

An apparatus and method for the reduction and fixation of a fracture is disclosed. The apparatus and method are described with respect to treating a proximal humeral fracture, although the apparatus and method are suitable for treating other types of fractures and fractures at other locations on the body. Treating a proximal humeral fracture during shoulder surgery includes reduction of the head out of varus or other malalignment and fixation of the shaft and head of the humerus. The apparatus and method is suitable for fractures where the plate can be secured to a bone and the mobile portion of the fracture is reduced with the jacking device. Such fracture types include tibial plateau and distal radius fractures.

Figure 1:
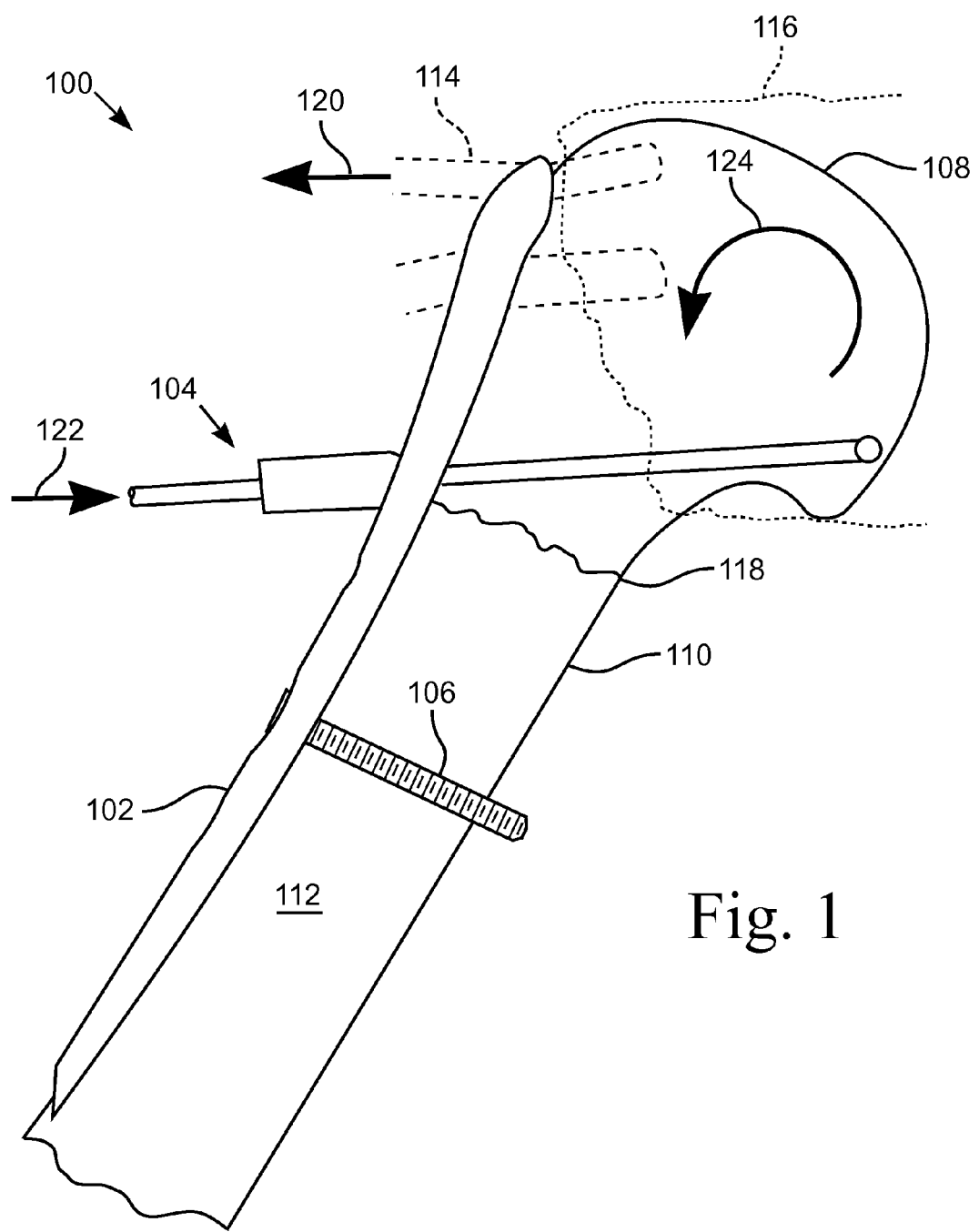
FIG. 1 is a side view of one embodiment of a jacking device and a locking plate at an initial stage of fixation.

FIG. 1 illustrates a side view of one embodiment of a fracture reduction and fixation device 100. The device 100 includes a jacking device 104 and a locking plate 102. The locking plate 102 is shown attached to the shaft 112 of a fractured humerus 110 with a screw 106. A jacking device 104 attached to the locking plate 102 engages an inferior aspect of the head 108. Suture material 114 is stitched in the teres minor, infraspinatus, supraspinatus, and/or subscapularis 116.

The illustrated embodiment shows the fracture 118 reduced such that the head 108 is aligned with the shaft 112. The jacking device 104 and the sutures 114 have rotated the head 108 to reduce the fracture 118. Pulling the suture material 114 results in an outward force 120 applied to the superior aspect of the head 108. The jacking device 104 applies an inward directed force 122 to the most inferior aspect of the head 108. The two forces 120, 122 impart a rotary motion 124 to the head 108 that moves the head 108 out of varus. Varus is the inward angulation of the humerus 110. In other embodiments, the jacking device 104 is positioned to move the head 108 in alignment when the head 108 is malaligned other than being in varus, for example, when the head 108 is in valgus.

Figures 2, 3A, 3B:
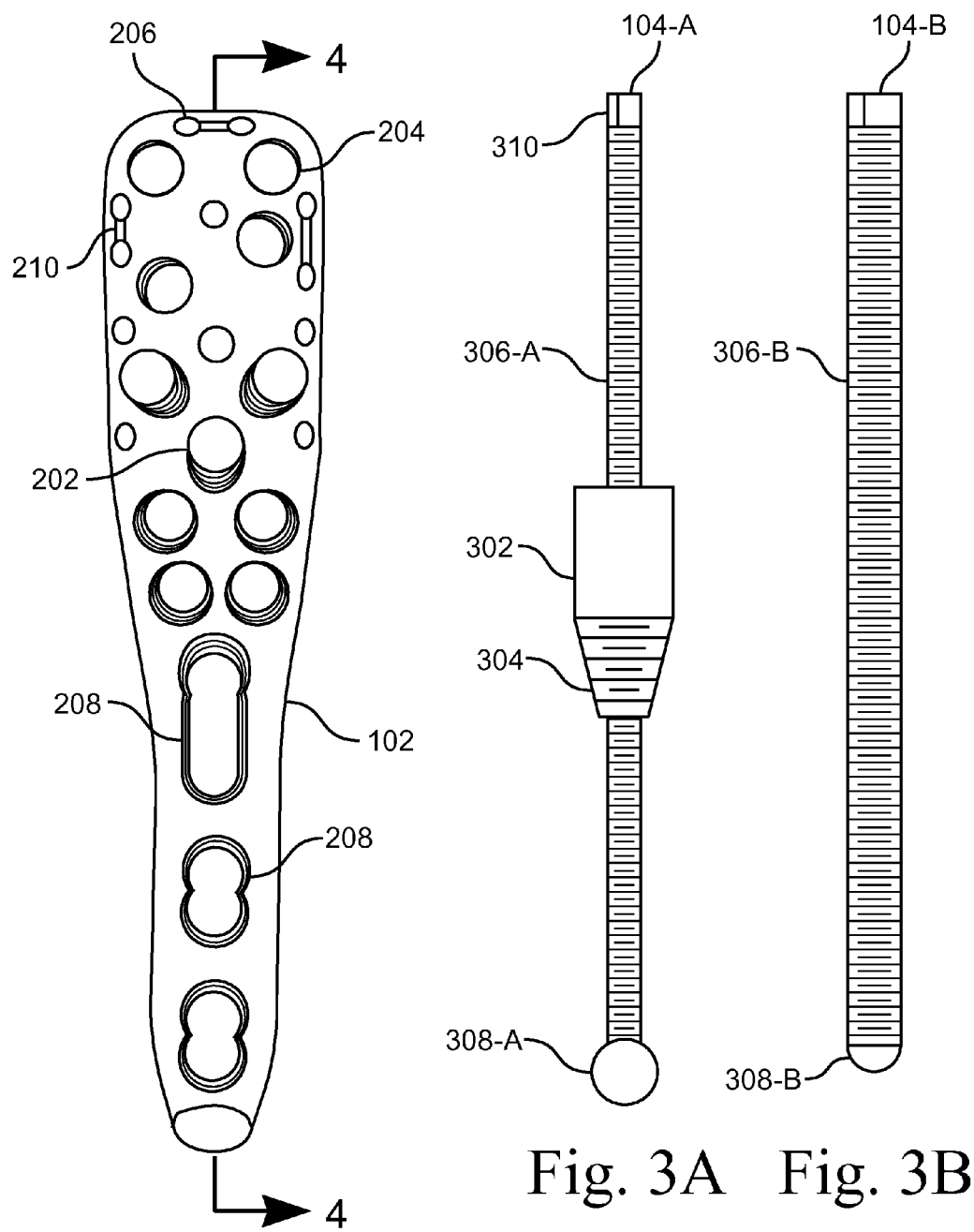
FIG. 2 is a plan view of one embodiment of a locking plate.
FIG. 3A is a plan view of one embodiment of a jacking device with a collar.
FIG. 3B is a plan view of another embodiment of a jacking device.

FIG. 2 illustrates a plan view of one embodiment of a locking plate 102. The locking plate 102 provides fixation of the fracture. The plate 102 includes an assortment of holes and openings 202, 204, 206. The plate 102 has a contoured-shape that allows the plate 102 to mate to the humerus 110. Further, the superior, or proximal, end of the plate 102 is wider than the inferior, or distal, end. The wider superior end accommodates the head 108, which is typically wider than the shaft 112.

The margins around the superior end of the plate 102 includes several pairs of suture holes 206. Each suture hole 206 is sized to receive suture material 114. In the illustrated embodiment, several of the pairs of suture holes 206 have a channel 210 between the two holes 206 of the pair. The channel 206 receives the suture material 114 and its knot to avoid the suture material 114 from protruding above the distal surface of the plate 102. One method of using the plate 102 uses the most superior suture holes 206 for the suture material 114 that is stitched to the supraspinatus muscle and uses the pairs of suture holes 206 on the upper sides of the plate 102 for the suture material 114 that is stitched to the infraspinatus, subscapularis, and/or teres minor.

The superior end of the plate 102 also includes locking, or threaded, holes 204 that receive locking screws 106. The locking holes 204 are threaded openings at various locations and at various angles to accommodate fixing the head 108 to the plate 102. Locking screws 106 are inserted through the locking holes 204 and into the head 106 to fix the head 108 to the locking plate 102. In various embodiments, one or more of the locking holes 204 are configured to receive a jacking device 104. In other embodiments, the holes 204 are configured to receive other fasteners, for example, non-locking screws or pegs.

The most inferior hole 202 at the superior end of the plate 202 is located adjacent the surgical neck. The inferior hole 202 is the jacking device hole, that is, it is the hole that receives the jacking device 104. The illustrated embodiment of the locking plate 102 shows that the jacking device hole 202 has an angle that positions the jacking device 104 at an inferior aspect of the head 108. In the illustrated embodiment, surrounding the hole 202 are other openings that are suitable for receiving a jacking device 104, for example, for an alternative location having a slightly different angle or for using a second jacking device 104.

The inferior end of the locking plate 102 includes a series of elongated holes 208 that are threaded. The elongated holes 208 receive screws 106, either locking or non-locking, that fix the shaft 112 to the plate 102. The most superior of the elongated holes 208 is configured to allow an extended superior-inferior translation of the plate 102 when the first screw 106 is used to initially attach the plate 102 to the shaft 112.

FIG. 3A illustrates a plan view of one embodiment of a jacking device 104-A. The jacking device 104-A includes a jacking screw 306-A and a collar 302. The jacking screw 306-A moves longitudinally through the collar 302 when the jacking screw 306-A is rotated, or screwed, about its longitudinal axis.

The jacking screw 306-A is an elongated member that is threaded. The distal end of the jacking screw 306-A includes a driver tip 310 that is configured to engage a driver. The driver rotates the jacking screw 306-A. In various embodiments, the driver is a manual, such as a knob or thumbscrew, or a powered rotary device that allows the jacking screw 306-A to be precisely located by screwing the jacking screw 306-A relative to the collar 302. The proximal end of the jacking screw 306-A includes a spherical end 308-A for engaging an inferior aspect of the head 108. In other embodiments, the proximal end of the jacking screw 306-A has other shapes for engaging the head 108, for example, a spiked or cupped end. The spherical end 308-A of the jacking screw 306-A is sized to pass through the jacking screw hole 202 in the plate 102.

The proximal end of the collar 302 includes a threaded fitting 304. The illustrated embodiment shows a threaded fitting 304 that has a conical thread that engages corresponding threads in a jacking device hole 202. In other embodiments the fitting 302 is configured to engage a hole 202, 204, 208 in the locking plate 102. In such embodiments, the threaded fitting 304 may not have threads that are conical. The collar 302 has a configuration that allows the collar 302 to be screwed into the plate 102 securely and to be removed from the plate 102 after fixation. For example, the distal end of the collar 302 has a slot for receiving a turning tool or the distal end has a hexagonal shape for engaging a turning tool.

FIG. 3B illustrates a plan view of another embodiment of a jacking device 104-B. The jacking device 104-B includes a jacking screw 306-B. The jacking screw 306-B moves longitudinally through a threaded opening 202 in the locking plate 102 when the jacking screw 306-B is rotated, or screwed, about its longitudinal axis.

The jacking screw 306-B is an elongated member that is threaded and the diameter of the screw 306-B is sized to fit in one of the threaded openings 202 in the locking plate 102. The illustrated embodiment of the jacking screw 306-B is configured to be extended past the plate 102 to engage the head 108 by rotating the screw 306-B.

The distal end of the jacking screw 306-B includes a driver tip 310 that is configured to engage a driver. The proximal end of the jacking screw 306-B includes a spherical end 308-B for engaging an inferior aspect of the head 108. The end 308-B is dimensioned such that the end 308-B will pass through the threaded opening 202 in the plate 102 when the jacking device 104-B is removed.

FIG. 1 illustrates the stage of shoulder surgery where reduction is complete with the head 108 out of varus and aligned with the shaft 112. The fracture 118 has been reduced and the humerus is ready for fixation. To achieve the illustrated reduction, sutures are placed in the rotator cuff 116. For example, inverted mattress stitches of a non-absorbable braided suture material 117 are placed in the teres minor, infraspinatus, supraspinatus, and/or subscapularis 116. The ends of the suture material 114 are passed through suture holes 206 in the plate 102. The plate 102 is then parachuted down onto the humerus 110. The plate 102 is then provisionally secured to the shaft 112 of the humerus 110 by a screw 106 inserted through an elongated hole 208 that allows for superior and inferior translation of the plate 102. Using a non-locking screw 106 allows the shaft 112 to be drawn tight against the plate 102. In the illustrated embodiment, the most superior elongated hole 208 is configured to allow the greatest superior and inferior translation. The other holes 208 are available for provisionally securing the shaft 112.

Pulling the suture material 117 away from the head 108 applies a force 120 away from the head. Screwing the jacking screw 306 into the collar 302 moves the proximal end 308 of the screw 306 inward and applies a force 122 to the inferior end of the head 108. The two forces 120, 122 apply a rotational force 124 to the head 108, thereby causing the head 108 to rotate in the direction of the force 124 and out of varus or other malalignment. The jacking screw 306 is shown in FIG. 1 with the tip 308 contacting the inside surface of the hard cortex of the head 108.

The fine threads of the jacking screw 306 allow the precise position and height of the head 108 to be dialed in to re-establish the anatomic neck/shaft angle. The head 108 is positioned by being pushed from the inferior aspect and pulled from one or more of the suture material 114 attached to the superior aspect of the head 108. The jacking device 104 rotates the head 108 in a plane, that is, the axis of rotation of the head 108 is perpendicular to the plane. Different sections of the suture material 114 are pulled with varying force to steer or guide the head 108 within the transverse plane. In various configurations, a second jacking device 104 is secured to the plate 102 to better position the head 108 and reduce the fracture.

When the desired position of the head 108 is achieved, the head 108 is secured to the plate 102. With the locking plate 102 securely fixed to the head 102, the jacking device 104 is removed from the plate 102. Additional locking screws 106 or other fasteners are then inserted through the elongated holes 208 and into the shaft 112.

Figure 4:
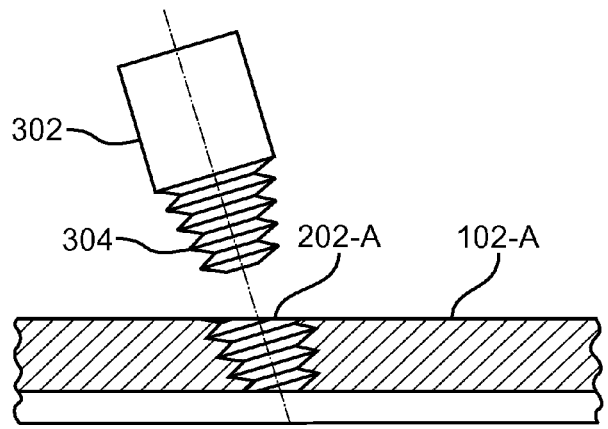
FIG. 4 is a partial cross-sectional view of one embodiment of a collar and a corresponding threaded opening.
Figure 6:
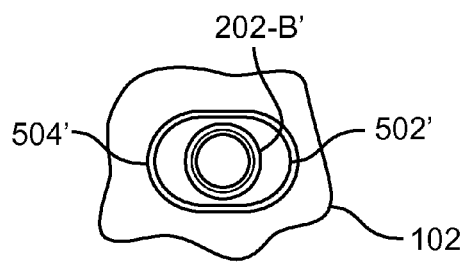
FIG. 6 is a partial top view of still another embodiment of the threaded opening.

FIG. 4 illustrates a partial cross-sectional view of one embodiment of a collar 302 and a corresponding threaded opening 202-A. The collar 302 includes a threaded fitting 304. In the illustrated embodiment, the threaded fitting 304 has conical threads that engage the corresponding threads in the jacking device hole 202-A. In the illustrated embodiment, the jacking device hole 202-A is formed in the locking plate 102 with an angle preset to direct the jacking screw 306 toward the inferior aspect of the head 108. In various embodiments, the jacking device hole 202-A is a single threaded opening as illustrated, one of several threaded openings grouped together, a multiple threaded opening, such as illustrated for the elongated holes 208 at the inferior end of the locking plate 102, or a variable angle screw fixation device, such as illustrated in FIGS. 6 and 6. The additional options for the jacking device hole 202-A allows for variations in the angle of the jacking screw 306.

Figure 5:
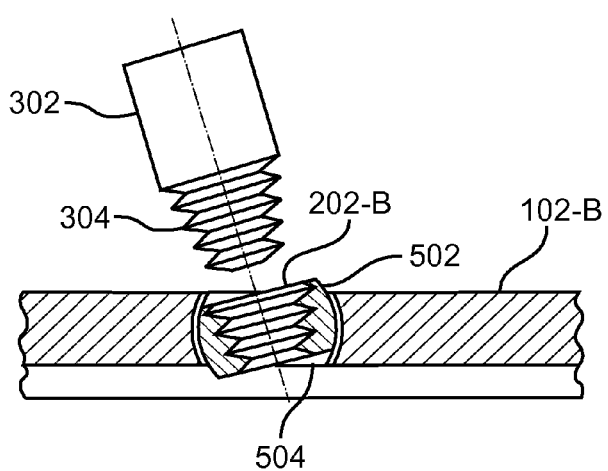
FIG. 5 is a partial cross-sectional view of another embodiment of a corresponding threaded opening.

FIG. 5 illustrates a partial cross-sectional view of one embodiment of a collar 302 and another embodiment of a corresponding threaded opening 202-B. The illustrated embodiment of the jacking device hole 202-B includes a swiveling plug, or bushing, 502 in a plug opening, or socket, 504. As shown in the longitudinal cross-section of FIG. 5, the swiveling plug 502 is spherical with a circular cross-section that is slightly smaller in diameter than the circular cross-section of the plug opening 504. Accordingly, the swiveling plug 502 rotates within the plug opening 504, thereby allowing the angle of the jacking device hole 202-B to be adjusted as needed. The concave sidewalls of the plug opening 504 hold the swiveling plug 502 captive in the opening 504. Axial pressure exerted by the jacking screw 306 when it engages the head 108 forces the outer surface of the swiveling plug 502 against the corresponding wall of the plug opening 504, and the frictional engagement minimizes unintentional angular movement of the jacking screw 306.

FIG. 6 illustrates a partial top view of another embodiment of the threaded opening 202-B' of FIG. 5. The swiveling plug 502' has a spherical shape with the lateral sides flattened. The plug opening 504' has a corresponding shape. The flattened sides of the swiveling plug 502' prevent the swiveling plug 502' from rotating when the threaded fitting 304 of the collar 302 is screwed into the jacking device hole 202-B'. Likewise, the flattened sides prevent the swiveling plug 502' from rotating when the jacking screw 306 is rotated. The flattened sides of the swiveling plug 502' are substantially parallel with the longitudinal axis of the locking plate 102, thereby allowing the angle of the jacking screw 306 to be adjusted in the coronal plane when the locking plate 102 is attached to the shaft 112.

Figure 7:
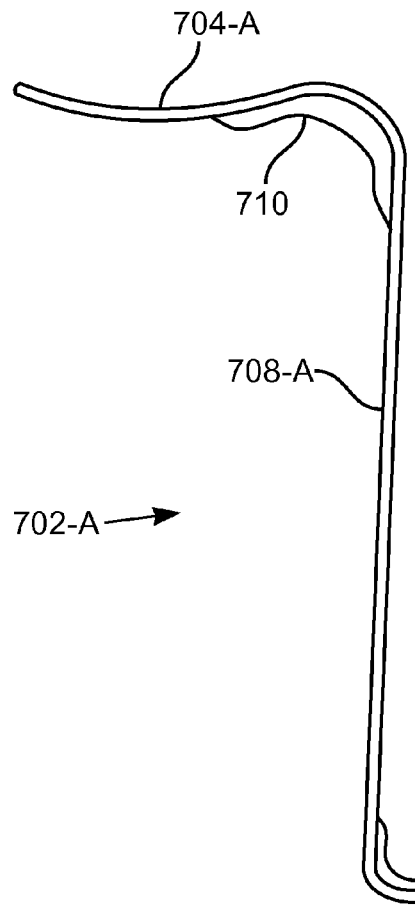
FIG. 7 is a side view of one embodiment of a radiolucent deltoid retractor.
Figure 8:
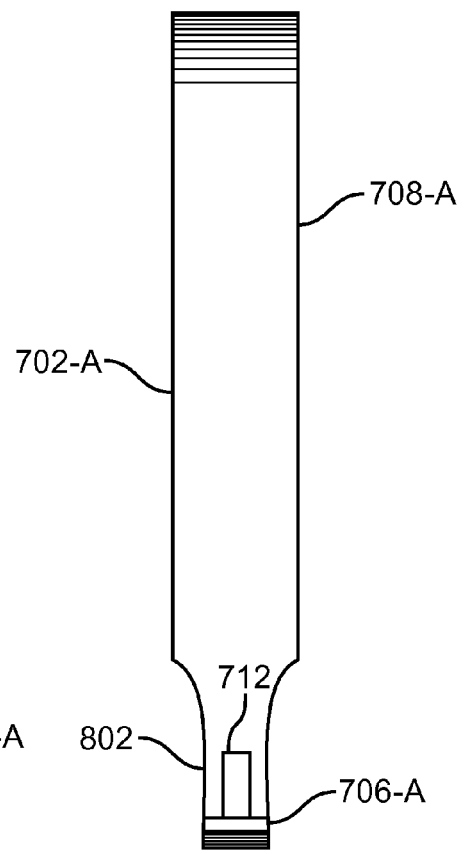
FIG. 8 is a front view of the radiolucent retractor of FIG. 7.

FIG. 7 illustrates a side view of one embodiment of a radiolucent deltoid retractor 702-A. FIG. 8 illustrates a front view of the radiolucent retractor 702-A of FIG. 7. The deltoid retractor 702-A includes a flat handle 704-A attached to an extension 708-A that terminates in a blade 706-A. The extension 708-A has a neck 802 that transitions the wider flat handle 704-A to the narrow blade 706-A. The retractor 702-A includes a handle rib 710 that reinforces the connection of the handle 704-A to the extension 708-A. The retractor 702-A also includes a blade rib 712 that reinforces the connection of the blade 706-A to the extension 708-A. The reinforcement ribs 710, 712 provide structural strength for the radiolucent material to withstand the pulling and levering forces applied to the retractor 702-A. In another embodiment, the edges of the blade 706-A are curved to accommodate the curved nature of the area, such as the deltoid, that is being manipulated.

Figure 9:
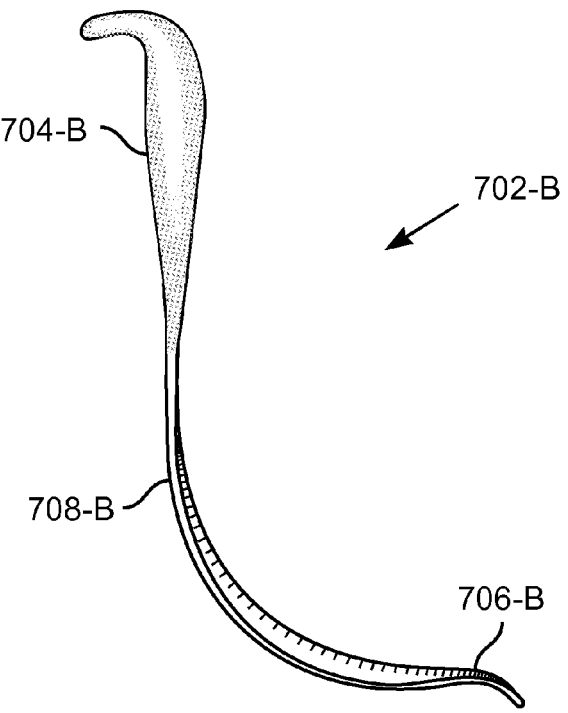
FIG. 9 is a perspective view of another embodiment of a radiolucent retractor.

FIG. 9 illustrates a perspective view of another embodiment of a radiolucent retractor 702-B. The retractor 702-B includes a rounded handle 704-B attached to a curved extension 708-B that terminates in a curved blade 706-B. The curved handle 704-B and the transition to the curved extension 708-B have a thickness that results in sufficient strength for the radiolucent material to withstand the pulling and levering forces applied to the retractor 702-B. The thickness and configuration of the curved blade 706-B is such that the radiolucent material withstands the forces applied to the curved blade 706-B.

Placing the locking plate 102, operating the jacking device 104, and placing the locking screws 106 requires working around the soft tissue of the patient's shoulder. To avoid stripping the tissue during the surgery, retractors 702 are used. Fluoroscopy is used to allow the surgeon to visualize the procedure in real-time. The illustrated retractors 702-A, 702-B are made of a radiolucent material that is transparent to the imaging rays of the fluoroscopic device. By being radiolucent, the retractor 702 does not block the surgeon's view of areas of interest. In another embodiment, the retractor 702 is made of two materials with the handle 704 being a first material and the blade 706 and a portion of the extension 708 being a second, radiolucent material. In this way only the portion of the retractor 702 that potentially would block the surgeon's view is made of a radiolucent material. In various embodiments, the first material is chosen for its strength, durability, grip, and/or characteristic other than being radiolucent.

Figure 10:
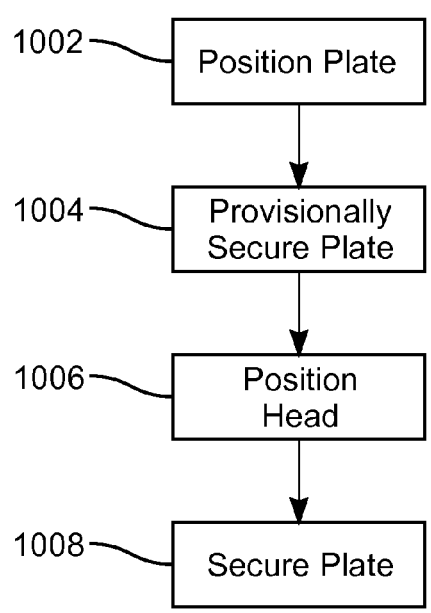
FIG. 10 is a block diagram of one embodiment of the steps for the method of reduction and fixation.

FIG. 10 illustrates a block diagram of one embodiment of the steps for the method of reduction and fixation. The illustrated method results in shorter surgery time for the patient and eliminates the need for provisionally reducing the fracture with multiple pins. The illustrated method also minimizes soft tissue stripping, thereby improving healing rates. Although the following steps are described with respect to the reduction and fixation of a proximal humeral fracture, the method is applicable to reducing and fixing other fractures.

The first step 1002 is to position the locking plate 102 adjacent the humerus 110 with the superior end of the plate 102 proximate the head 108. For a deltopectoral approach, suture material 114 is stitched to the tissue adjacent the superior aspect of the head 108. The suture material 114 is then passed through the appropriate suture holes 206 in the locking plate 102. The plate 102 is then parachuted down onto the humerus 110. In one such embodiment, inverted mattress stitches of a non-absorbable braided suture material, such as #2 Fiber-wire, are placed in the supraspinatus, infraspinatus, subscapularis, and/or teres minor.

The next step 1004 is to provisionally secure the plate 102 to the shaft 112 of the humerus 110. In one embodiment, a non-locking screw 106 is inserted through an elongated hole 208 that provides for superior and inferior translation of the plate 102. The non-locking screw 106 is placed in the shaft 112 with the plate 102 at an appropriate height relative to the humerus 110. The height or position of the plate 102 relative to the humerus 110 is changed by loosening the screw 106 and translating the plate 102 along the humerus 110.

The next step 1006 is to position the head 108 out of varus or other malalignment and in alignment with the locking plate 102. The positioning step 1006 includes attaching the jacking device 104 to the plate 102, positioning the jacking screw 306 such that the proximal end 308 is angled up into an inferior aspect of the head 108, and adjusting the jacking screw 306 to apply a force 122 to a non-yielding surface of the head 108. Positioning the jacking screw 306 to contact the most inferior aspect of the head 108 provides maximum leverage for rotating the head 108, although other positions are suitable for use. If there is no communication or hole for the jack screw 306 to pass through the cortex of the humerus 110, the cortex is perforated with a drill, such as one used for the locking screws 106.

After being positioned, the jacking device 104 is operated to advance the jacking screw 306. At the same time the suture material 114 is pulled to guide or steer the head 108 into position adjacent the superior end of the locking plate 102. The jacking screw 306 is rotated to dial in the appropriate head height to reestablish the anatomic neck/shaft angle.

In one embodiment, reducing the fracture includes viewing the shaft 112, head 108, and the fracture reduction and fixation device 100 with a fluoroscopic or other imaging device. That is, the positioning step 1006 is performed under fluoroscopic guidance. The imaging device provides a representation or visualization of the relative positions of the bone fragments 112, 108 and the jacking device 104. During the step 1006 of positioning the head 108 to reduce the fracture, manual manipulation with a retractor 702 may be required. The retractor 702 allows the joint, including the soft tissue around the head 108, to be manipulated and the retractor 702 aids in positioning the head 108, along with pulling the suture material 114 and advancing the jacking screw 306. In order to allow the imaging device to operate without being blocked by the retractor 702, a radiolucent material is used for the blade 706. The imaging device's view of the jacking device 104 is not blocked by the blade 706 when the blade 706 is inline with the jacking device 104 and the imaging device.

The next step 1008 is to secure the locking plate 102 to the humerus 110. With the head 106 positioned, screws 106 are inserted through the holes 204 and into the head 108. The jacking device 104 is removed after the head 108 is secured to the locking plate 102. The suture material 114 is tied. In the embodiment with the channels 210, the suture material 114 is tied and positioned in the appropriate channel 210. The securing step 1008 also includes securing the shaft 112 to the locking plate 102 with screws 106 or other fasteners.

The illustrated method is also suitable for being performed with a superior approach. With the superior approach, the screws and/or pegs can be placed with guides or percutaneously.

The fracture reduction and fixation device 100 includes various functions. The function of jacking is implemented, in one embodiment, by the jacking device 104 as illustrated in FIG. 3. The function of selecting an angle of attack for the jacking device 104 is implemented, in various embodiments, by the jacking device hole 202 as illustrated in FIGS. 2, 4, 5, and 6.

The function of adjusting the angle of the elongated member, or jacking screw, 306 relative to the plate 102 is implemented, in one embodiment, by a bushing 502 movable within a socket 504 in the plate 102. The function of preventing rotation of the bushing 502' within the socket 504' is implemented, in one embodiment, by the bushing 502' having an oblong shape that cooperates with a corresponding socket 504'.

The function of allowing an imaging device to see the shaft 112, head 108, and the fracture reduction and fixation device 100 when reducing the fracture with manual manipulation is implemented, in one embodiment, by a retractor 702 having a radiolucent blade, or tip, 706.

From the foregoing description, it will be recognized by those skilled in the art that a fracture reduction and fixation device 100 has been provided. The fracture reduction and fixation device 100 includes a plate 102 and a jacking device 104. The plate 102 includes an assortment of holes and openings 202, 204, 206 and the jacking device 104 engages any one of them. The holes and openings 202, 204, 206 variously are locking and/or non-locking openings with fixed and/or variable angles. The jacking device 104 is positioned to progressively apply pressure to the head 108 to aid in rotating the head 108 to reduce the fracture. The plate 102 also includes suture holes 106 through which suture material 114 is threaded to aid in rotating the head 108, along with the jacking device 104. With the plate 102 fixed to the bone shaft 112 the fracture is reduced by operation of the jacking device 104 and the suture material 114. When the fracture is reduced, the plate 102 is fixed to the head 108.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A method for reducing and fixing a fracture, said method comprising the steps of:
   a) position a distal portion of a plate against a bone shaft with a portion of said plate proximate the fracture and a proximal portion of said plate proximate a head;
   b) provisionally secure said distal portion of said plate to said bone shaft;
   c) reduce said fracture by rotating said head out of varus and into alignment with said shaft by performing the steps of
      c1) advancing an elongated member attached to said plate to push a first aspect of said head, and
      c2) pulling on suture material that is threaded through soft tissue attached to a second aspect of said head, said suture material threaded though openings in said proximal portion of said plate; and
   d) after said fracture is reduced, secure said proximal portion of said plate to said head and secure said distal portion of said plate to said bone shaft.

2. The method of claim 1 wherein step c) of reducing said fracture further includes a step of adjusting an insertion angle of said elongated member such that a proximal tip of said elongated member is positioned to contact a non-yielding surface of said head.

3. The method of claim 1 wherein step c) of reducing said fracture further includes a step of adjusting an insertion angle of said elongated member such that a proximal tip of said elongated member is positioned into an inferior aspect of said head.

4. The method of claim 1 wherein step c) of reducing said fracture further includes a step of attaching a jacking device to said plate, said jacking device including said elongated member.

5. The method of claim 1 wherein step c) of reducing said fracture further includes a step of manually manipulating with a retractor having a blade that is radiolucent.

6. The method of claim 1 wherein said step d) of securing said plate includes inserting a plurality of fasteners into corresponding openings in said plate, said plurality of fasteners attaching said plate to said bone shaft and said head.

7. The method of claim 1 further including, after said step d) of securing said plate, a step of removing said elongated member from said plate.

8. A method for reducing and fixing a fracture, said method comprising the steps of:
   a) position a plate against a shaft of bone wherein the fracture is located medially between a proximal portion and a distal portion of said plate, said plate being positioned with said distal portion proximate said shaft and with said proximal portion of said plate proximate a head;
   b) provisionally secure said distal portion of said plate to said shaft;
   c) reduce the fracture by performing the steps of
      c1) advancing a jacking device to push a first aspect of said head, and
      c2) pulling on suture material that is threaded through soft tissue attached to a second aspect of said head, said suture material threaded though openings in said proximal portion of said plate; and
   d) after said fracture is reduced, secure said proximal end of said plate to said head and secure said distal end of said plate to said bone shaft.

9. The method of claim 8 wherein said step c) of reducing the fracture includes rotating the head out of varus and into alignment with said shaft by pushing with said jacking device and pulling with said suture material whereby said head is rotated into alignment with said shaft.

10. The method of claim 8 further including, before said step c1) of advancing said jacking device, a step of adjusting an insertion angle of said jacking device such that a proximal tip of said jacking device is positioned to push against a non-yielding surface of said head.

11. The method of claim 8 wherein said step d) of securing said plate includes inserting a plurality of fasteners into corresponding openings in said plate, said plurality of fasteners attaching said plate to said bone shaft and to said head.

12. The method of claim 8 further including, after said step d) of securing said plate, a step of removing said jacking device from said plate.

13. A method for reducing and fixing a fracture, said method comprising the steps of:
   a) select a plate sized and configured to extend from a head to a shaft with the fracture positioned medially relative to said plate, said plate configured to receive a jacking device;
   b) provisionally secure a distal end of said plate to said shaft such that a proximal end of said plate is proximate the head;
   c) after said plate is provisionally secured, position a jacking device extending from said plate such that a proximal end of said jacking device is positioned to push against a first aspect of said head;
   d) after said plate is provisionally secured, thread suture material through soft tissue attached to a second aspect of said head and through a plurality of openings in said proximal end of said plate;
   e) after said jacking device is positioned and said suture material is threaded, reduce the fracture by rotating said head out of varus and into alignment with said shaft; and
   f) after the fracture is reduced, secure said proximal end of said plate to said head and secure said distal end of said plate to said shaft.

14. The method of claim 13 wherein step a) of selecting a plate includes a step of selecting said plate such that said jacking device extends from a proximal surface of said plate such that said proximal end of said jacking device is positionable to engage said first aspect of said head.

15. The method of claim 13 wherein step a) of selecting a plate includes a step of selecting said plate with said plurality of openings positioned proximate a peripheral edge of said proximal end of said plate and with said plurality of openings arranged in pairs and being sized and dimensioned to receive suture material.

16. The method of claim 13 wherein said step e) of reducing the fracture includes advancing said jacking device to push said first aspect of said head and by pulling said suture material to move said second aspect of said head toward said proximal end of said plate, thereby causing said head to rotate out of varus and into alignment with said shaft.

17. The method of claim 13 wherein step e) of reducing said fracture further includes a step of adjusting an insertion angle of said jacking device such that said proximal end of said jacking device is positioned to push against a non-yielding surface of said head.

18. The method of claim 13 wherein step e) of reducing said fracture further includes a step of manually manipulating with a retractor having a blade that is radiolucent.

19. The method of claim 13 wherein said step f) of securing said plate includes inserting a plurality of fasteners into corresponding openings in said plate, said plurality of fasteners attaching said plate to said bone shaft and said head.

20. The method of claim 13 further including, after said step f) of securing said plate, a step of removing said jacking device from said plate.

\* \* \* \* \*